United States Patent [19]

Steffan

[11] 4,404,033

[45] Sep. 13, 1983

[54] METHOD OF MAKING COLLAGEN FIBERS FOR SURGICAL USE

[75] Inventor: Wolfgang Steffan, Neustadt/Donau, Fed. Rep. of Germany

[73] Assignee: CHEMOKOL Gesellschaft zur Entwicklung von Kollagenprodukten, Stolberg, Fed. Rep. of Germany

[21] Appl. No.: 358,025

[22] Filed: Mar. 15, 1982

Related U.S. Application Data

[63] Continuation-in-part of Ser. No. 267,776, May 28, 1981, abandoned.

[30] Foreign Application Priority Data

[DE] Fed. Rep. of Germany ....................

[51] Int. Cl.$^3$ .................... A23J 1/10; C08L 89/00; D06M 3/02
[52] U.S. Cl. .................... 106/161; 260/123.7; 28/166; 8/127.5
[58] Field of Search .................... 106/161; 260/123.7; 28/166

[56] References Cited

U.S. PATENT DOCUMENTS

| | | | |
|---|---|---|---|
| 2,838,363 | 6/1958 | Veis et al. | 106/124 |
| 3,114,372 | 12/1963 | Griset et al. | 128/335.5 |
| 3,114,593 | 12/1963 | Griset et al. | 264/103 |
| 3,366,440 | 1/1968 | Nuwayer | 8/115.6 |
| 3,374,103 | 3/1968 | Barkin | 106/161 |
| 3,511,904 | 5/1970 | Griset | 264/202 |
| 3,520,402 | 7/1970 | Nichols et al. | 206/59 |
| 3,527,225 | 9/1970 | Smith | 128/335.5 |
| 3,625,811 | 12/1971 | Sato et al. | 128/335.5 |
| 3,742,955 | 7/1973 | Battista et al. | 128/334 R |
| 4,185,011 | 1/1980 | Eckmayer | 260/123.7 |
| 4,295,894 | 10/1981 | Cioca et al. | 106/161 |

FOREIGN PATENT DOCUMENTS

2730623 9/1979 Fed. Rep. of Germany.

OTHER PUBLICATIONS

Chem. Abst. 81: 107,384, Balabanaova et al, 1973.

*Primary Examiner*—Theodore Morris
*Attorney, Agent, or Firm*—Brooks, Haidt, Haffner & Delahunty

[57] ABSTRACT

A method is provided for the manufacture of collagen fibers for surgical purposes, in which Achilles tendons or hides from cottle are decomposed in an alkaline medium and are mechanically treated after treatment with an acid, deswelled, crosslinked and dried, wherein that Achilles tendons are decomposed in an alkaline medium to an amino-nitrogen content of from 0.15 to 0.30 $\mu$moles/g and after a hydrochloric acid treatment and washing to a pH value of from 2 to 4, the swollen collagen substance is reduced in thickness under pressure forming a two-dimensional network, then the individual longitudinal fibers are exposed by hackling, and then, after deswelling, the fibers are cross-linked with hexamethylene diisocyanate in the presence of a nonionic or cationic emulsifier and are dehydrated and further processed on textile machines.

7 Claims, No Drawings

METHOD OF MAKING COLLAGEN FIBERS FOR SURGICAL USE

This is a continuation-in-part of copending Steffan application Ser. No. 267,776 filed May 28, 1981, now abandoned.

The invention deals with a process of manufacturing collagen fibers for surgical applications using Achilles tendons or hides as starting material.

Isolation of collagen fibers for surgical applications as sutures or in the form of hemostatic fleece or as wound dressing material and other uses has been known. In the above surgical applications it is important that the collagenous material, specifically the collagen fibers, retain their native structure. For this reason the method of isolation and purification of collagen fiber from the starting material should extract all noncollagenous components of the original tissue without denaturing the original crystalline structure of collagen. Unless it is dictated by medical reasons, there should not be any noncollagenous contaminants present in the final pure collagen fiber.

Several patents describe the method of isolating microfibrillar collagen as a hemostatic agent or reconstituting surgical structures from solubilized collagen gels.

According to the Battista patent (U.S. Pat. No. 3,742,955) a fluffy, finely divided microfibrils of collagen are produced. The length of the fibrils, amounting to an average of 100 $\mu$m, does not allow further textile processing.

Several other patents refer to procedures resulting in complete disintegration of the fibrillar structure of collagen. By their process, a gel of dispersed collagen molecules is reconstituted by a complex process into fibrillar form by an extrusion into a precipitating medium. (Veis et al, U.S. Pat. No. 2,838,363; Smith, U.S. Pat. No. 3,527,225; Grisef et al, U.S. Pat. Nos. 3,114,372 or 3,114,593 or 3,511,904; Nichols et al, U.S. Pat. No. 3,520,402). The process according to the Barkin patent (U.S. Pat. No. 3,374,103) uses mammalian tendons sliced to 10 to 25 mils thick sections. This step by itself prevents isolation of long fibers as is the original feature of this invention. Thus, the Barkin process must also employ extrusion of acid swollen collagen solution to form continuous filaments.

Neither of the patents by Highterger et al (U.S. Pat. Nos. 2,934,446 and 2,934,467) result in isolated and parallel oriented collagen fibers which could be processed by textile technology. The collagen fibers obtained by the above cited patents are randomly oriented, forming a sheet of interlocked collagen fiber masses.

In summary, none of the total prior art teach or suggest, in whole or in part, either individually or in combination, the original features of this invention as disclosed and claimed herein. In these processes the original fibrillar structure of collagen is completely lost and the collagen exists as monomer or dimer in a viscous solution which is extruded and precipitated into a continuous artificial collagen fiber. Our invention deals not with reconstituted collagen but with isolated and purified collagen fibers from the starting material.

The patent DE-PS 27 30 623 describes another method of preparation of collagen fibers. This process starts with skin or skin trimmings or tendons treated with alkali or acids. Minced starting material is first exposed to strong alkali and swollen in the next step in acid environment. The swollen material is then washed and water removed mechanically by a press and chemically by various salts or organic solvents to form 20 to 40 weight % dry substance. This material then serves to isolate the fibers. Contrary to the statement of the above cited patent that the isolated collagen fibers are free, loose, not forming knots, the practice shows that the process results in imperfect solubilization of collagenous material into separate fibers and in high proportion of noncollagenous materials present mainly in the nodes of insoluble structures. The presence of nodes, amorphous material and also short fibers interferes with further processing of this material into products such as yarn, fabric, fleece using the standard textile technology requiring separate, loose fibers of adequate length of more than 3 cm.

It is the object of this invention to describe a process of making collagen fibers for surgical use when the isolated fibers are loose—not forming knots or nodes. Another aim of this invention is to treat the collagen material in such a way that the resulting fibers are easily processed by various machinery used by the textile industry. Yet another aim of this invention is to describe the modifications of the resulting fibers needed to obtain yarn, fleece or fabrics.

In our invention the starting material are Achilles tendons. Especially Achilles tendons or hides from cattle contain long collagen fibers oriented in the longitudinal array in both wet or dry state; the diameter of these fibers, can be further mechanically split into fibrils, still oriented in a parallel manner.

Alkali treatment of Achilles tendons or hides lasts until the material contains 0.15 to 0.30 $\mu$moles amide nitrogen/g dry weight. This range of values is essential for the following processing of collagen. This range of values of this invention is also different from that claimed in DE-PS 27 30 623 where the alkali treatment results in collagen with amide nitrogen from 0.30 to 0.40 $\mu$moles/g. This invention stresses the importance of proper content of amide nitrogen of collagen as the value refers to the structural stability of this fibrillar protein. It also refers to the purity of collagen freed from all noncollagenous contaminants. The treatment with alkali is done by any of known methods, such as with calcium hydroxide, in which case, the incubation lasts up to six weeks. Another known method is treatment with sodium hydroxide in the presence of sodium sulfate, which shortens the treatment period to two to five days.

It is advantageous, during the alkali treatment of the Achilles tendons or hides, to expose this material to fluted roller, in which the tendons or hides are dehydrated and compressed. After alkali treatment resulting in collagen with 0.15 to 0.30 $\mu$moles amide nitrogen/g the material is washed with hydrochloric acid. While it is possible to use other organic or inorganic acids to wash the alkali-treated tendons, it is with advantage to use hydrochloric acid as during the neutralization formed sodium chloride is from physiologic point of view more acceptable than other salts. During the treatment with hydrochloric acid, some other noncollagenous components, such as glycosaminoglycans, are extracted. At the same time, the original, rather compact fibers of the tendons or hides are loosened. It is recommended to control that during the treatment with hydrochloric acid the pH of the tendonds or hides through the whole thickness of the bundle is acidic, reaching pH less than 2.

After acid treatment, the material is washed in tap water until the pH of the tendons is 2 to 4, with preference between pH 2.5 to 3.5. So far the alkali treatment, acid incubation and washing to a defined pH were described. The next step is the mechanical treatment. The washed, swollen collagen paste is exposed to mechanical stress of fluted rollers. During this procedure, the collagen fibers are isolated and separated from the gluing effect of soluble and denatured collagens and, at the same time, the fibers are partly dehydrated. The mechanical treatment results in transforming the three-dimensional structure of the tendons to a two-dimensional layer network which still has a certain thickness. This compressed and partially dehydrated layer is now processed through hackling which separates individual fibers without changing their parallel orientation. It is advantageous to repeat the treatment with hackling for instance two to five times with continuously increasing comb intensity during each successive treatment.

The result of hackling is the separation of parallel oriented fibers from the bundle of the tendon structure. Dehydration of these individual fibers in the next step uses various salts or change of pH to the isoelectric pH of collagen to pH 4.5 to 7.0, preferably to 5.5 to 6.5. Neutralization, viz dehydration due change of pH results in fibers with lower elasticity, pliability than when dehydration is achieved with salts such as sodium chloride or sodium sulfate. For reasons stated above, it is preferable to use sodium chloride. Another advantage of using sodium chloride is its easy extractability during the following steps, as described below. The optimal concentration of sodium chlorided use for dehydration is between 5 to 15 weight percent. The released fluid is then removed for instance by centrifugation or by any other method separating the solid phase from the fluid.

Dehydrated fibers are now tanned to reduce or eliminate their swelling in water and the antigenicity. This step also makes the textile processing possible, as described below.

Several tanning agents have been employed to cross-link collagen used in various medical applications or in the leather industry. Experiments showed, however, that tanning with aldehydes, for example with formaldehyde or glutaraldehyde, as is the case of DE-PS 27 30 623 is inadequate, leaving cytotoxic residues of the aldehyde within the collagen matrix. The tanning with hexamethylene diisocyanate was found to be the optimal, resulting in fibers acceptable from both medical-toxicologic and technical-textile processing point of view.

The tanning takes place in aqueous solution of salts used for dehydration of collagen fibers. In this case the fluid separated from the fibers by salts is not removed. In case it was removed, an appropriate volume of water is added to the fibers.

The tanning with hexamethylene diisocyanate (HMDIC) occurs in the presence of nonionic or cationic detergents and in stoichiometric excess of this tanning agent. In practice, the concentration of HMDIC is 10 to 20 weight percent of collagen dry substance. The tanning is a rather slow process and the reaction time is 10 to 40 hours, optimally 15 to 30 hours. Side products formed during the tanning, such as hexamethylene diamine, as well as excess of detergent and the stillabundant presence of salt are removed during dehydration of fibers by separating the fluid and by drying the resulting tanned collagen fibers.

Dehydration and drying of collagen fibers is achieved by known procedures. Collagen fibers are dried in the presence of various water-mixable organic solvents with low boiling points. Still, aceton dehydration showed in the practice to be the most advantageous.

The dried and tanned longitudinally parallel oriented collagen fibers are now processed by special textile machinery. To those familiar with the art of textile processing, it is clear that special properties of collagen fibers should be taken into consideration when selecting the adequate machinery. To the expert it is known, for instance, that cotton is processed by different equipment than wool.

This invention results in collagen fibers substantially longer than those prepared by other procedures. The fiber length is 40 mm to 100 mm and the diameter is between 30 to 80 μm. This contrasts with collagen prepared according to Battista (U.S. Pat. No. 3,742,955) where the average length of the fibers is 100 Å. This length is too short to allow further textile processing as described by this invention.

The above described procedures indicate that the method constituting this invention to prepare collagen fibers for surgical uses consists of several consecutive steps, some of the individual steps being part of a common knowledge, but the specific sequence of these individual steps and adherence to specific conditions which leads to a product with unique properties representing substantial improvement over the existing knwon methods. The unique properties refer to long collagen fibers without the presence of knots or nodes, free of contaminating antigenic substances, the fibers subjected with ease to further textile processing.

In order that those skilled in the art may better understand how the present invention may be carried out, the following example is given by way of illustration and not by way of limitation.

EXAMPLES

Example 1

All information about percent or volume content relates to wet weight of the tendon-collagen material.

Dissected Achilles tendons from calf are washed, mechanically cleaned of adhering fat, then washed again. Approximately 250 g of tendons with 30 percent dry weight can be obtained from one calf.

Washed tendons are now incubated for 8 days at 20° C. in a solution consisting of 20% sodium sulfate, 2% sodium hydroxide and 150% water. Two, four and six days after the incubation the tendons are mechanically treated between fluted rollers. On day 8 the tendons are thoroughly washed in tap water. The remaining tendons contain 0.23 μmoles amide nitrogen/g of tissue.

In the next step the tendons are transferred into a tanning drum and treated with hydrochloric acid. The sample contains 100% water and 10% of hydrochloric acid (diluted to 3%). The acid treatment lasts approximately 4 hours. The tendons are then washed in tap water to obtain pH 2.7 to 3.3 through all the thickness of the tendons which now have the dry weight of 14%.

Slightly swollen tendons are now exposed to the high pressure of a hammer press, under which treatment the excess water as well as soluble and denatured-nonstructured proteins are removed. The swollen and compressed tendons have the appearance of a two-dimensional fibrillar network layer. This layer is now treated with hackling in three successive steps with increasing pressure exerted on the fibrous layer.

The resulting separated fibers are now treated with 10 parts per weight of sodium chloride and 100 parts per weight of water for 16 hours. During this, the water formed by the dehydration process is then removed by centrifugation.

In the next step, the deswollen material is incubated in the presence of 5% solution of sodium chloride (100% related to wet weight of fibers). A nonionic detergent at 1% final concentration is mixed with the fibers and pH is adjusted with sodium hydroxide to pH 6.0. After 30 minutes of mixing, hexamethylene diisocyanate is added to form 5% of the wet weight of the fibers. The treatment with this tanning agent lasts 30 hours under continuous mixing in the drum. The toxic vapors are removed. After this treatment the liquid is removed by centrifugation.

In the next step the now cross-linked material is dehydrated with 100 weight percent of aceton. This step is repeated four times. Dehydrated fibers are dried in the air filtered through bacteriological filters to minimize eventual contamination with airborne bacteria.

Fibers are dissociated on a carding machine. The carding machine consists of a precarder equipped with two or three places of action covered with a saw-toothed card clothing. The main carder is attached next to the precarder with five places of action equipped with a flexible card clothing. By using a special card towards each other a good untangling of the fibers can be reached. At the end of the machine a card web is formed. By doubling (folding) of this card web any thickness can be manufactured. An improvement of the card web and the fleece regarding their uniformity can be acquired through additional carding work with finer clothing and a more narrow adjustment. The card web, doubled into a fleece, can be processed on an embossing roller into a tight sheet. The fleece acquired this way (still untanned and without cross-linking) show an excellent hemostatic effect.

In order to fabricate yarn from the dissociated collagen fibers, one parts the fibrous mass which was treated as described above ('untangled' on a carding machine and made into a card web) into individual bands or threads with the help of a card web divider. The fiber bands acquired thereby are twisted with rubs and are formed into a preyarn, which does not show any strength yet. The preyarn is stretched and twisted on condensing ring spinning frame. The number of the yarn twists depend mostly on the intended yarn strength and fiber length.

The yarn usually shows many fiberends sticking out from the fiber core making it very difficult to weave or knit the fibers. Therefore, the yarn is moistened and run through rubbing leathers to attach the fiber ends back to the main fibers. The fibers are now ready to be made into fabrics or knitted goods with the usual methods.

Example 2

The neck fissures of cattle hides (without scar tissue and without subcutaneous connective tissue) are treated in the manner of the leather industry (softening, liming, depilating, fleshing, skiving). This is followed by the additional alkaline treatment, the aim of which is to free the collagen from physiologically undesirable impurities. In addition the hide pieces are treated for 25 days with saturated $Ca(OH)_2$ solution and 0.1% sodium hydroxide solution (batch to material solution ratio is 1:3).

The material is stirred thoroughly every day several times. Thereby the fatty residue is saponified and the accompanying proteins are treated and washed out. Afterwards the material is washed with fresh running water. The amide nitrogen value is now 0.27 mmol/gr. After washing, treatment with 2% hydrochloric acid is carried out. The material is treated for four hours, while being moved. After this period the hides are completely acidified, which is checked by the use of a pH paper. Washing with cold flowing water follows. After about 2 hours, the pH value of the material in full thickness is 3.0 and the dry content is 13.8% by weight. The hides treated chemically in this way are now cut into pieces of $10 \times 10$ cm. Pressing between grooved rollers follows, and is repeated up to 8 times. The fibrous pieces are now placed in a 20% solution of common salt for shrinking. This process can be clearly observed due to the change in color (from a glassy to a white color). After shrinkage, the salt liquid is centrifuged off from the fiber pieces and the substance is dehydrated with acetone whereby three times 150% by weight of acetone, based on the measured weight of the fibrous substance is used after hydroextraction. Then the fiber pieces are dried in the open air and are processed into fleeces, which has already been described in detail in example 1.

What is claimed is:

1. In a method for the manufacture of collagen fibers for surgical purposes, in which a starting material selected from the group consisting of Achilles tendons and hides from cattle is decomposed in an alkaline medium and are mechanically treated after treatment with an acid, deswelled, cross-linked and dried, the improvement comprising the steps of:

decomposing said starting material in an alkaline medium to an amino-nitrogen content of from 0.15 to 0.30 $\mu$moles/g and after a hydrochloric acid treatment and washing to a pH value of from 2 to 4, the swollen collagen substance is reduced in thickness under pressure forming a two-dimensional network, then the individual longitudinal fibers are exposed by hackling, and then, after deswelling, the fibers are cross-linked with hexamethylene diisocyanate in the presence of a nonionic or cationic emulsifier and are dehydrated and further processed on textile machines.

2. Process according to claim 1, wherein the thickness reduction of the swollen collagen substance is carried out by using a hammer press or a calendering machine or by fluted rollers.

3. Process according to claim 1, wherein the shrinking of the fibers is carried out by the use of a sodium chloride solution of from 5 to 50% by weight, preferably 7 to 15% by weight.

4. Process according to claim 1, wherein an impregnation with medicaments at the same time as the dehydration of said fibers is carried out.

5. Process according to claim 1, 2, 3 or 4, wherein the collagen fibers are processed on modified carding machines to fiber fleeces of any desired weight and then by pressing with embossing rollers are solidified into firm textile flat shaped articles.

6. Process according to claim 1, 2, 3 or 4, wherein the collagen fibers are processed on modified carding machines to fiber fleeces of any desired weight and then by pressing with embossing rollers are solidified and wherein the solidified fiber fleece is processed to fiber yarn very similar to carded yarn, whereby said fibers protruding from the yarn are pieced by a subsequent treatment into a pair of rubbing leathers, and the yarns thus prepared are processed on conventional textile machines into fabrics.

7. Process according to claim 2, wherein the shrinking of the fibers is carried out by the use of a sodium chloride solution of from 5 to 50% by weight, preferably 7 to 15% by weight.

* * * * *

UNITED STATES PATENT AND TRADEMARK OFFICE
CERTIFICATE OF CORRECTION

PATENT NO. : 4,404,033
DATED : September 13, 1983
INVENTOR(S) : Wolfgang Steffan It is certified that error appears in the above—identified patent and that said Letters Patent is hereby corrected as shown below:

On the title page, the line following item [30] should read:

-- May 30, 1980 [DE] Fed. Rep. of Germany.... 3020611 --.

Signed and Sealed this

Tenth Day of July 1984

[SEAL]

Attest:

GERALD J. MOSSINGHOFF

Attesting Officer

Commissioner of Patents and Trademarks